United States Patent
Dixon et al.

(10) Patent No.: US 9,804,376 B2
(45) Date of Patent: Oct. 31, 2017

(54) SCANNER WITH INCREASED DYNAMIC RANGE

(71) Applicant: HURON TECHNOLOGIES INTERNATIONAL INC., Waterloo, Ontario (CA)

(72) Inventors: Arthur Edward Dixon, Waterloo (CA); Savvas Damaskinos, Kitchener (CA)

(73) Assignee: Huron Technologies International Inc., Waterloo (CA)

( * ) Notice: Subject to any disclaimer, the term of this patent is extended or adjusted under 35 U.S.C. 154(b) by 318 days.

(21) Appl. No.: 14/382,277

(22) PCT Filed: Mar. 4, 2013

(86) PCT No.: PCT/CA2013/000191
§ 371 (c)(1),
(2) Date: Aug. 29, 2014

(87) PCT Pub. No.: WO2013/126999
PCT Pub. Date: Sep. 6, 2013

(65) Prior Publication Data
US 2015/0109432 A1    Apr. 23, 2015

Related U.S. Application Data

(60) Provisional application No. 61/606,245, filed on Mar. 2, 2012.

(51) Int. Cl.
*H04N 9/47* (2006.01)
*H04N 7/18* (2006.01)
(Continued)

(52) U.S. Cl.
CPC ....... *G02B 21/008* (2013.01); *G01N 21/6456* (2013.01); *G02B 21/0076* (2013.01);
(Continued)

(58) Field of Classification Search
CPC .......................... G02B 21/008; G02B 21/367; G02B 21/0076; G01N 21/6456; G01N 21/6458; G01N 2021/6417
(Continued)

(56) References Cited

U.S. PATENT DOCUMENTS

2005/0270638 A1* 12/2005 Soenksen ............ G02B 21/002
                                                  359/368
2008/0297597 A1* 12/2008 Inomata ................... G03B 7/00
                                                   348/80
(Continued)

*Primary Examiner* — Jared Walker
(74) *Attorney, Agent, or Firm* — Daryl W. Schnurr

(57) ABSTRACT

An instrument and method for scanning all or part of a large specimen mounted on a specimen holder takes a plurality of measurements of each pixel in the whole or part of the specimen being scanned at a plurality of exposure values. A computer controls the movement of the specimen holder during scanning and again of the detector to produce a digitized image of all or part of the specimen with larger dynamic range than the dynamic range of the detection system. In a further embodiment, the instrument can scan two successive, identical strips at a different exposure values and combine the images from the two scans into one digitized image having a larger dynamic range than the dynamic range of the detection system.

17 Claims, 12 Drawing Sheets

(51) Int. Cl.
   *G02B 21/00*     (2006.01)
   *G01N 21/64*     (2006.01)
   *G02B 21/36*     (2006.01)

(52) U.S. Cl.
   CPC ....... *G02B 21/367* (2013.01); *G01N 21/6458* (2013.01); *G01N 2021/6417* (2013.01)

(58) Field of Classification Search
   USPC ..................................................... 348/79–80
   See application file for complete search history.

(56) References Cited

U.S. PATENT DOCUMENTS

| | | | | |
|---|---|---|---|---|
| 2009/0072171 | A1* | 3/2009 | So ...................... | G06K 9/00127 250/584 |
| 2010/0253774 | A1* | 10/2010 | Yoshioka ............... | G02B 21/16 348/79 |
| 2010/0274496 | A1* | 10/2010 | Hummel ............ | G01N 21/6408 702/19 |
| 2012/0205519 | A1* | 8/2012 | Mohler .................... | G01J 1/20 250/206 |

\* cited by examiner

SCANNER WITH INCREASED DYNAMIC RANGE

BACKGROUND OF THE INVENTION

Field of the Invention

This invention relates to the fields of confocal and non-confocal imaging of large microscope specimens with particular emphasis on fluorescence and photoluminescence imaging systems, including multi-photon fluorescence, spectrally-resolved fluorescence, and second and third harmonic imaging. Applications include imaging tissue specimens, genetic microarrays, protein arrays, tissue arrays, cells and cell populations, biochips, arrays of biomolecules, detection of nanoparticles, photoluminescence imaging of semiconductor materials and devices, and many others.

Description of the Prior Art

FIG. 1 shows one embodiment of a prior art confocal scanning laser macroscope, as described in U.S. Pat. No. 5,760,951. In this embodiment, the incoming collimated laser beam 102 from laser 100 passes through a beam expander (comprised of lens 104 and lens 106), and is expanded to match the diameter of entrance pupil 112 of laser scan lens 114 (note—entrance pupil 112 as indicated on FIG. 1 simply indicates the position of the entrance pupil. A real stop is not placed at this position). Scanning mirror 110 deflects the beam in the X direction. Laser scan lens 114 focuses the beam to focused spot 116 on specimen 118, mounted on microscope slide 120, and light reflected from or emitted by the specimen is collected by laser scan lens 114, descanned by scanning mirror 110, and partially reflected by beamsplitter 108 into a confocal detection arm comprised of laser rejection filter 130, lens 132, pinhole 134, and detector 136. Detector 136 is located behind pinhole 134. Light reflected back from focused spot 116 on specimen 118 passes through pinhole 134 and is detected, but light from any other point in the specimen runs into the edges of the pinhole and is not detected. The scan mirror is computer-controlled to raster the focused spot across the specimen. At the same time, microscope slide 120, which is mounted on a computer-controlled, motor-driven scanning stage 122, moves slowly in the Y direction. The combination of rapid beam scanning across the specimen while it is moved slowly in the perpendicular Y direction results in a raster-scan motion of focused-laser spot 116 across specimen 118. A computer, represented by computer screen 140, is connected to detector 136 to store and display a signal from detector 136. The computer provides means for acquiring, manipulating, displaying and storing the signal from the detector. This confocal macroscope has properties similar to those of a confocal scanning laser microscope, except that the field of view of the microscope is much smaller.

The instrument shown in FIG. 1 has the ability to adjust the gain of the detector depending on the fluorescence intensity of the fluorophore, and a high-speed preview scan can be used to predict the exposure required for each fluorophore before scanning the final high-resolution image (see PCT application WO 2009/137935 A1). Because the laser scan lens has a wide field of view, large specimens can be scanned in a few wide strips, making it possible to scan very large specimens (up to 6×8 inches in size in one version of a commercial instrument).

Several other technologies are used for fluorescence imaging of large specimens. With tiling microscopes, the image of a small area of the specimen is recorded with a digital camera (usually a CCD camera), the specimen is moved with a computer-controlled microscope stage to image an adjacent area, an image of the adjacent area is recorded, the stage is moved again to the next area, and so on until a number of image tiles have been recorded that together cover the whole area of the specimen. Images of each area (image tiles) are recorded when the stage is stationary, after waiting long enough for vibrations from the moving stage to dissipate, and using an exposure time that is sufficient to record the fluorescence images. These image tiles can be butted together, or overlapped and stitched using computer stitching algorithms, to form one image of the entire specimen.

When tiling microscopes are used for fluorescence imaging, the areas surrounding each tile and the overlapping edges of adjacent tiles are exposed twice (and the corners four times) which can bleach some fluorophores. Exposure can be adjusted by varying the exposure time for each tile. If multiple fluorophores are imaged, a different exposure time is required for each, so each fluorophore requires a separate image at each tile position. Multiple exposure of the specimen for imaging multiple fluorophores can also increase bleaching of the fluorophores.

A prior art strip-scanning microscope for fluorescence imaging is shown in FIG. 2. A tissue specimen 202 (or other specimen to be imaged) mounted on microscope slide 201 is illuminated from above by illumination source 203. In fluorescence imaging the illumination source is usually mounted above the specimen (epifluorescence) so that the intense illumination light that passes through the specimen is not mixed with the weaker fluorescence emission from the specimen, as it would be if the illumination source were below the specimen. Several different optical combinations can be used for epifluorescence illumination—including illumination light that is injected into the microscope tube between the microscope objective and the tube lens, using a dichroic beamsplitter to reflect it down through the microscope objective and onto the specimen. A narrow wavelength band for the illumination light is chosen to match the absorption peak of the fluorophore in use. Fluorescence emitted by the specimen is collected by infinity-corrected microscope objective 215 which is focused on the specimen by piezo positioner 220. Emission filter 225 is chosen to reject light at the illumination wavelength and to pass the emission band of the fluorophore in use. The microscope objective 215 and tube lens 230 form a real image of the specimen on TDI detector array 240. An image of the specimen is collected by moving the microscope slide at constant speed using motorized stage 200 in a direction perpendicular to the long dimension of TDI detector array 240, combining a sequence of equally-spaced, time-integrated line images from the array to construct an image of one strip across the specimen. Strips are then assembled to form a complete image of the specimen. When a CCD-based TDI array is used, each line image stored in memory is the result of integrating the charge generated in all of the previous lines of the array while the scan proceeds, and thus has both increased signal/noise and amplitude (due to increased exposure time) when compared to the result from a linear array detector. Exposure can be increased by increasing illumination intensity and/or by reducing scan speed. It is difficult to predict the best exposure before scanning. When multiple fluorophores are used on the same specimen, the usual imaging method is to choose illumination wavelengths to match one fluorophore, select the appropriate emission filter and scan time (speed) for the chosen fluorophore, and scan one strip in the image. Then the illumination wavelength band is adjusted to match the absorption band of the second fluorophore, a matching emission filter and scan speed are chosen, and that strip is scanned again. Additional fluorophores require the same steps to be repeated. Finally, this sequence is repeated for all strips in the final image. Some instruments use multiple TDI detector arrays to scan multiple fluorophores simultaneously, but because all fluorophores are scanned at the same scan speed, this usually results in a final image where one fluorophore is exposed correctly and the others are either under- or over-exposed. Exposure can be adjusted by changing the relative intensity of the excitation illumination for each fluorophore, which should be easy to do if LED illumination is used. When multiple illumination bands are used at the same time, the resulting image for each fluorophore may differ from that produced when only one illumination band is used at a time because of overlap of the multiple fluorophore excitation and emission bands, and because autofluorescence from the tissue itself may be excited by one of the illumination bands. Autofluorescence emission usually covers a wide spectrum and may cause a bright background in all of the images when multiple fluorophores are illuminated and imaged simultaneously.

A good description of strip scanning instruments, using either linear arrays or TDI arrays, is given in US Patent Application Publication # US2009/0141126 A1 ("Fully Automatic Rapid Microscope Slide Scanner", by Dirk Soenksen).

When a strip-scanning instrument using either a linear array or TDI detector is used for fluorescence imaging, the fluorescence exposure is measured in advance, often by scanning the entire specimen and then using the resulting image to set scan speed and illumination intensity before making the final scan. When imaging specimens with multiple fluorophores, exposure for each fluorophore is measured separately. If exposure is not measured in advance, the result is often over- or under-exposed images.

Fluorescent specimens often emit a wide range of fluorescence intensity, which may require a wider dynamic range than the detection system can measure, even if the best exposure is set in advance. This is similar to the problem of photographing landscapes where the image brightness ranges from deep shadows through mid-tones to the bright sky with white clouds, and where detail must be preserved both in the shadows and in the clouds. In photography, HDR (High Dynamic Range) imaging is achieved by capturing several images of the same scene at different exposures, and merging them into the same image. Portions of the source images showing most detail are given most weighting in the merge process. A digital camera using this method is described in U.S. Pat. No. 5,828,793 ("Method and Apparatus for Production of Digital Images having Extended Dynamic Range", by Steve Mann). A similar technique for scanning fluorescence microscope slides is described in U.S. Patent Application #US 2009/0238435 A1 ("Multi-Exposure Imaging for Automated Fluorescent Microscope Slide Scanning", by Kevin Shields). In both of these descriptions, multiple source images with different exposures are combined to produce a single image in which detail is preserved in dark, mid-tone and bright areas of the image, but relative pixel intensities are not preserved across the image.

A different method for capturing a high dynamic range image of a specimen is described in U.S. Patent Application #US 2011/0134280 A1 "System and Method for Constructing High Dynamic Range Images" by Chou et al. In this method, a first image of the specimen is processed to generate illumination parameters that are then used to modulate the incident light intensity used for imaging various areas of the specimen, resulting in a composite image in which the illumination in different areas of the specimen has been varied to preserve detail in those areas of the image, but relative pixel intensities are not preserved across the image.

Definitions

For the purposes of this patent document, a "macroscopic specimen" (or "large microscope specimen") is defined as one that is larger than the field of view of a compound optical microscope containing a microscope objective that has the same Numerical Aperture (NA) as that of the scanner described in this document.

For the purposes of this patent document, "fluorescence" includes but is not limited to single-photon excitation, two-photon and multiphoton fluorescence, spectrally-resolved fluorescence, and photoluminescence; and "specimen" includes but is not limited to tissue specimens, genetic microarrays, protein arrays, tissue arrays, cells and cell populations, biochips, arrays of biomolecules, plant and animal material, insects and semiconductor materials and devices. Specimens may be mounted on or contained in any kind of specimen holder. "Fluorophores" include synthetic fluorophores, fluorescent proteins, and quantum dots. "Autofluorescence" is fluorescence from endogenous molecules, like proteins in a tissue specimen.

For the purposes of this patent document, "exposure" means any combination of illumination intensity, scan speed (which when increased reduces dwell time for spot-scanning systems) or shutter speed (for linear detector arrays, e.g. CCD arrays or CMOS arrays).

Detector gain can be adjusted by changing PMT voltage and/or preamplifier gain in a spot-scanning instrument, or signal gain in an instrument using array detectors.

For the purposes of this patent document, TDI or Time Delay and Integration is defined as a method and detectors used for scanning moving objects, usually consisting of a CCD-based detector array in which charge is transferred from one line of pixels in the detector array to the next in synchronism with the motion across the detector array of a real image of the moving object. As the real image moves as a result of motion of the object, charge builds up as it is transferred from one line of pixels in the array to the next, and the result is charge integration similar to a longer exposure used with stationary imaging. When the image of one line on the object (and integrated charge) reaches the last row of the array, that line of pixels is read out. In operation the last line of pixels from the moving image is read out continuously, creating one row of pixels in the final mage at a time. One example of such a camera is the DALSA Piranha TDI camera.

"Contract" is defined as dynamic range contraction.

A "multispectral" image is one that contains data from several discrete and narrow detection bands. For example, when multiple fluorophores are imaged, the signal from each fluorophore is detected using a narrow-band detection filter. When these images are combined into a single image, it is a "multispectral" image. (No spectra are recorded, only data from a few narrow and discrete detection bands.)

When a spectrally-resolved detector is used to record the spectrum of fluorescence emission from a spot on a specimen, and the data from each spot on the specimen (each pixel position) are combined into an image, such an image is a "hyperspectral" image, and a fluorescence spectrum of each image pixel is measured at that pixel position on the specimen.

A "scan lens" is a colour-corrected and infinity-corrected lens with an external entrance pupil. A mirror scanner can be placed at the external entrance pupil position without requiring any intermediate optics between the mirror scanner and the scan lens. A "laser scan lens" is a scan lens designed for use with laser light sources, and is usually not colour-corrected.

For the purposes of this patent document, a sparse-pixel preview image is an image of at least part of a specimen comprised of equally-spaced pixels that have the same size and exposure as pixels in a final image of the same area of the specimen.

SUMMARY OF THE INVENTION

An instrument for scanning at least a part of a large specimen mounted on a specimen holder comprises a light source, at least one lens to focus light from the light source, a detection system that comprises at least one detector, and a computer. The computer is programmed and configured to:
a) take a plurality of measurements of each pixel at a plurality of exposure values;
b) receive, process and store data received from the at least one detector;
c) control a power output of the light source; and
d) control the movement of the specimen holder during scanning and a gain of the at least one detector to produce a digitized image of the at least one part of the specimen with a larger dynamic range than a dynamic range of the detection system.

An instrument for scanning at least a part of a large specimen mounted on a specimen holder comprises scanning means, a detection system having at least one detector, and a computer. The computer is programmed and configured to:
a) cause the instrument to scan a full strip at one exposure and to scan the identical strip at another exposure;
b) combine the two images from the two scans into one digitized image of the at least part of the scanned specimen; and
c) the digitized image having a larger dynamic range than a dynamic range of the detection system.

A method of scanning at least a part of a specimen mounted on a specimen holder uses an instrument comprising of scanning means, a detection system having at least one detector and a computer programmed and configured to operate the instrument. The method comprises:
a) taking a plurality of measurements of each pixel in the at least part of the specimen being scanned at a plurality of exposure values; and
b) controlling the movement of the specimen holder during scanning and a gain of the detector to produce a digitized image of that part of the scanned specimen with a larger dynamic range than a dynamic range of the detection system.

OBJECTS OF THE INVENTION

1. It is an object of this invention to provide a method and instrument for scanning a large microscope specimen on a glass microscope slide (or other specimen holder) that results in a digitized image with an increased dynamic range that is large enough to display image detail in dark, mid-range and bright areas of the image where the method of combining scan lines preserves relative pixel intensities across the entire image, and where the final image has a larger dynamic range than the dynamic range of the detection system of the instrument.
2. It is an object of this invention to provide a method and instrument for scanning a large microscope specimen on a glass microscope slide (or other specimen holder) in fluorescence that results in a digitized image with an increased dynamic range that is large enough to display image detail in dark, mid-range and bright areas of the image where the method of combining scan lines preserves relative pixel intensities across the entire image, and where the final image has a larger dynamic range than the dynamic range of the detection system of the instrument.
3. It is an object of this invention to provide a method and instrument for scanning a large microscope specimen on a glass microscope slide (or other specimen holder) in two-photon or multi-photon fluorescence that results in a digitized image with an increased dynamic range that is large enough to display image detail in dark, mid-range and bright areas of the image where the method of combining scan lines preserves relative pixel intensities across the entire image, and where the final image has a larger dynamic range than the dynamic range of the detection system of the instrument.
4. It is an object of this invention to provide a method and instrument for scanning a large microscope specimen on a glass microscope slide (or other specimen holder) in fluorescence that results in a digitized image with an increased dynamic range that is large enough to display image detail in dark, mid-range and bright areas of the image while preserving relative pixel intensities across the image, where sequences of adjacent scan lines with different exposure are detected and the data from each sequence of adjacent scan lines are combined to provide data for a single line of increased dynamic range data in the final image.
5. It is an object of this invention to provide a method and instrument for scanning a large microscope specimen on a glass microscope slide (or other specimen holder) in fluorescence that results in a digitized image with an increased dynamic range that is large enough to display image detail in dark, mid-range and bright areas of the image while preserving relative pixel intensities across the image, where the increased dynamic range is large enough that a plurality of microscope slides can be scanned without requiring changes in instrument setup before scanning each slide.
6. Same as Object 2 where the method is to acquire sequences of adjacent scan lines in which each scan line has an increased exposure compared to the exposure of the previous line. For example, with two lines in each sequence, the illumination intensity of line two can be equal to twice the illumination intensity of line one, by doubling the intensity of the light source). As a second example, the scan time of the second line can be made twice as long as the first, resulting in a pixel dwell time in the second line that is twice as long as the first, so twice as many photons are collected for each pixel in the second line. In situations of increased exposure it is likely that some pixels in line two are saturated, but contrast in areas with weak fluorophores will be higher in line two than in line one. Pixel data from line one is multiplied by a factor and pixel data from lines one and two are combined to produce a single line of pixels in the final image, comprised of pixel data from line 1 multiplied by the factor when the value is larger than a chosen amount, and pixel data from line 2 are used at or below this value.
7. Same as Objects 1-6 above but where the exposure values are chosen using high-speed preview scans of the entire specimen as described in PCT application WO 2009/137935 A1, where the preview scans are comprised of sparse pixel images of equally-spaced pixels (that have the same size as corresponding pixels in the final image) across at least part of the area of the specimen.

8. If the final image is to have one micron pixels (for example), and a two-line sequence is used, then pixels in each scan line should be one micron apart, but scan lines should be spaced ½ micron apart. (It is usually easiest to keep the scanning stage moving at a constant speed instead of stopping and collecting two scan lines at each position). For best results, in a situation where two exposure values are used and the scanning stage moves at a constant speed, pairs of sequential odd-numbered scan lines can be averaged on a pixel-by-pixel basis before being combined with the even-numbered scan line between them.

9. Adjacent scan lines using a sequence of three exposures can also be used—for example, if a sequence of exposures where the exposure is varied in a sequence approximating 1×, 2× and 4×, then data in scan line 1 is multiplied by $f_1$, data in scan line 2 is multiplied by $f_2$, and data in scan line 3 is multiplied by $f_3$, where $f_1$ and $f_2$ are factors that multiply line 1 and line 2 data to fit the intensity curve of data values in line 3 before combination of the linescan data, and where $f_1 > f_2 > f_3$ and $f_3 = 1.0$. After combination of the linescan data, data from line 1 represent the brightest areas of the image, data from line 2 represent the mid-range and data from line 3 represent the weakest fluorescence areas.

10. Exposure can be controlled by modulating the illumination source intensity while scanning, so that line one is at 1 mW, line two at 2 mW, line three back to 1 mW, etc.; or line one at 1 mW, line two at 2 mW, line three at 4 mW, line four back to 1 mW, etc. (This example assumes laser sources—of course other sources like LED's, etc. can also be used.)

11. Same as above (Objects 1-10) but using one or more linear array detectors (used in scanners like that shown in FIG. 2) instead of single-pixel detectors (like the photomultiplier tube which is often used in point scanners like that shown in FIG. 1), except that when using linear array detectors exposure values are chosen using one or more linescans on the specimen or a scan of at least part of the specimen instead of the high-speed preview scans described in Object 7. A sparse pixel image cannot be efficiently created when using a linear detector.

12. It is an object of this invention to provide a method and instrument for scanning a large microscope specimen on a glass microscope slide (or other specimen holder) in spectrally-resolved fluorescence that results in a digitized image from each detector channel with an increased dynamic range that is large enough to display image detail in dark, mid-range and bright areas of the image where the method of combining scan lines preserves relative pixel intensities across the entire image, and where the final image has a larger dynamic range than the dynamic range of the detection system of the instrument.

13. It is an object of this invention to provide a method for contracting dynamic range where contraction of individual image tiles is performed by software on a serving computer when serving the image tiles, and where dynamic range contraction is based on one or more regions of interest. The image can then be viewed using all or substantially all of the dynamic range of a remote computer display, while dynamic range of the image data in the original file is preserved. When a region of interest is specified, the dynamic range for viewing this region of interest is specified by the remote computer and contraction parameters are calculated by the serving computer. This calculation can be based on a histogram of the region of interest calculated from data in the original image file, and can be performed automatically to match the dynamic range of the histogram to the dynamic range of the remote computer display, or the user can adjust the dynamic range by specifying changes and viewing the result on the computer display. Viewing software contracts each tile as it is viewed on the computer containing the original high dynamic range image file.

14. It is an object of this invention to provide a method for contracting dynamic range and serving image tiles over a network where contraction of individual image tiles is performed on the server just before sending these image tiles out over the network, and where dynamic range contraction is based on one or more regions of interest, or on the entire image file. The image can then be viewed on a remote computer using all or substantially all of the dynamic range of the remote computer display, while dynamic range of the image data in the original file is preserved. When a region of interest is specified from the remote computer, contraction parameters for this region of interest are calculated by the server and these parameters are used when viewing any portion of this region of interest on the remote computer. This calculation can be based on a histogram of the region of interest, and can be performed automatically to match the dynamic range in the histogram to the dynamic range of the remote display, or the user can adjust the dynamic range by specifying changes in the contraction parameters and viewing the result on his remote computer display. By specifying changes in the contraction parameters, the viewer can specify the range of intensity values to be viewed. When serving image tiles from the pyramidal image file to the remote computer, software on the server contracts each tile as it is served to the remote computer. Images can be viewed on the display attached to the scanning instrument or over a network on the displays of one or more remote computers. The term "remote computer" includes cell phones, tablets, laptops and other computers with image display capability appropriate for the image being displayed. On first connection to the server, the remote computer informs the server of its display capabilities (which can be accomplished by sending the make and model number of a cell phone, tablet or laptop, or an instrument-specific file for other display computers) and dynamic-range contraction by the server before serving image tiles is based on this information. If the color space used by the remote computer is different from that of the stored image file, the server can convert the color space of each tile before serving to match that of the remote computer display.

15. It is an object of this invention to provide a method for re-creating or reviewing a viewing session on a remote computer. For later review, the region of interest specification, dynamic range contraction and color space parameters and information describing which tiles were served and the order of serving can be stored on the remote computer or on the server. This allows the viewing session to be re-created at a later time (perhaps for medical consult or review), or a new viewing session to be performed using the same region of interest and viewing parameters.

DESCRIPTION OF THE INVENTION

Figure 1:
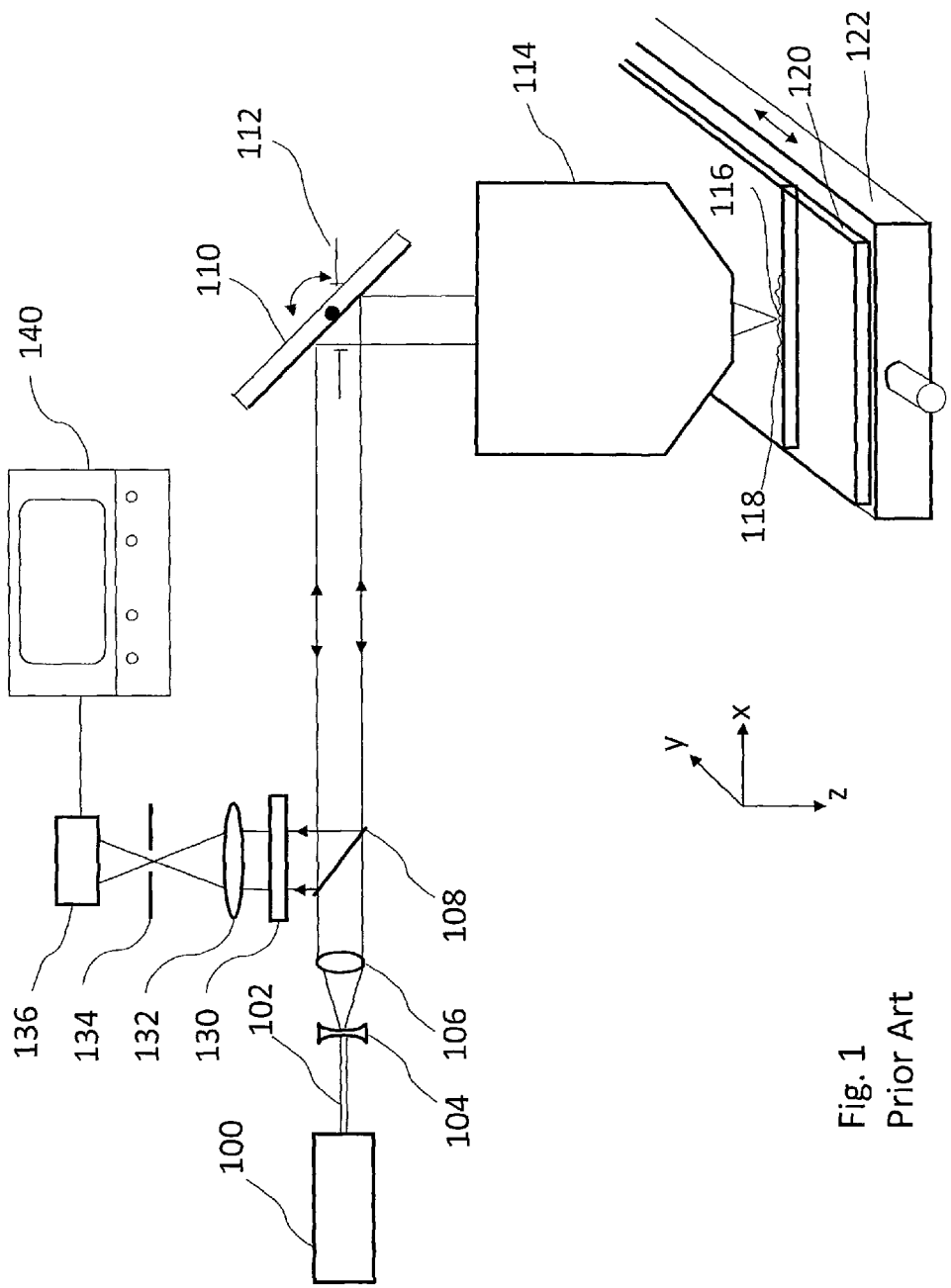
FIG. 1 is a schematic view of a prior art confocal scanning-beam/scanning-stage optical macroscope (a scanning-spot instrument)
Figure 2:
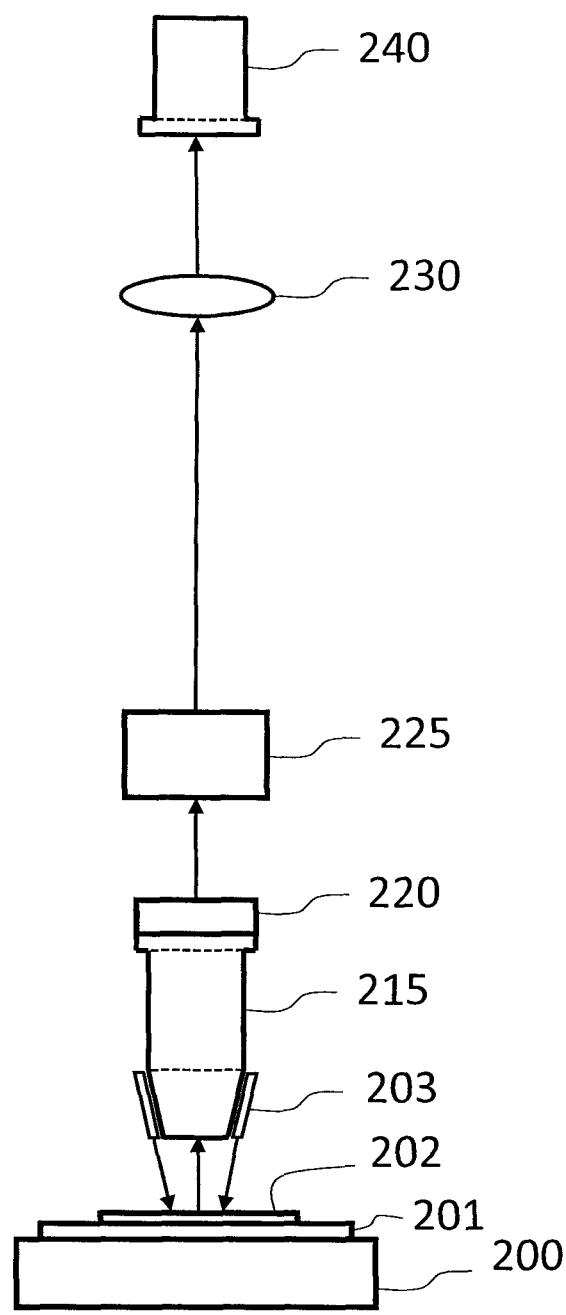
FIG. 2 is a schematic view of a prior art fluorescence microscope slide scanner using a linear or TDI detector array.
Figure 3:
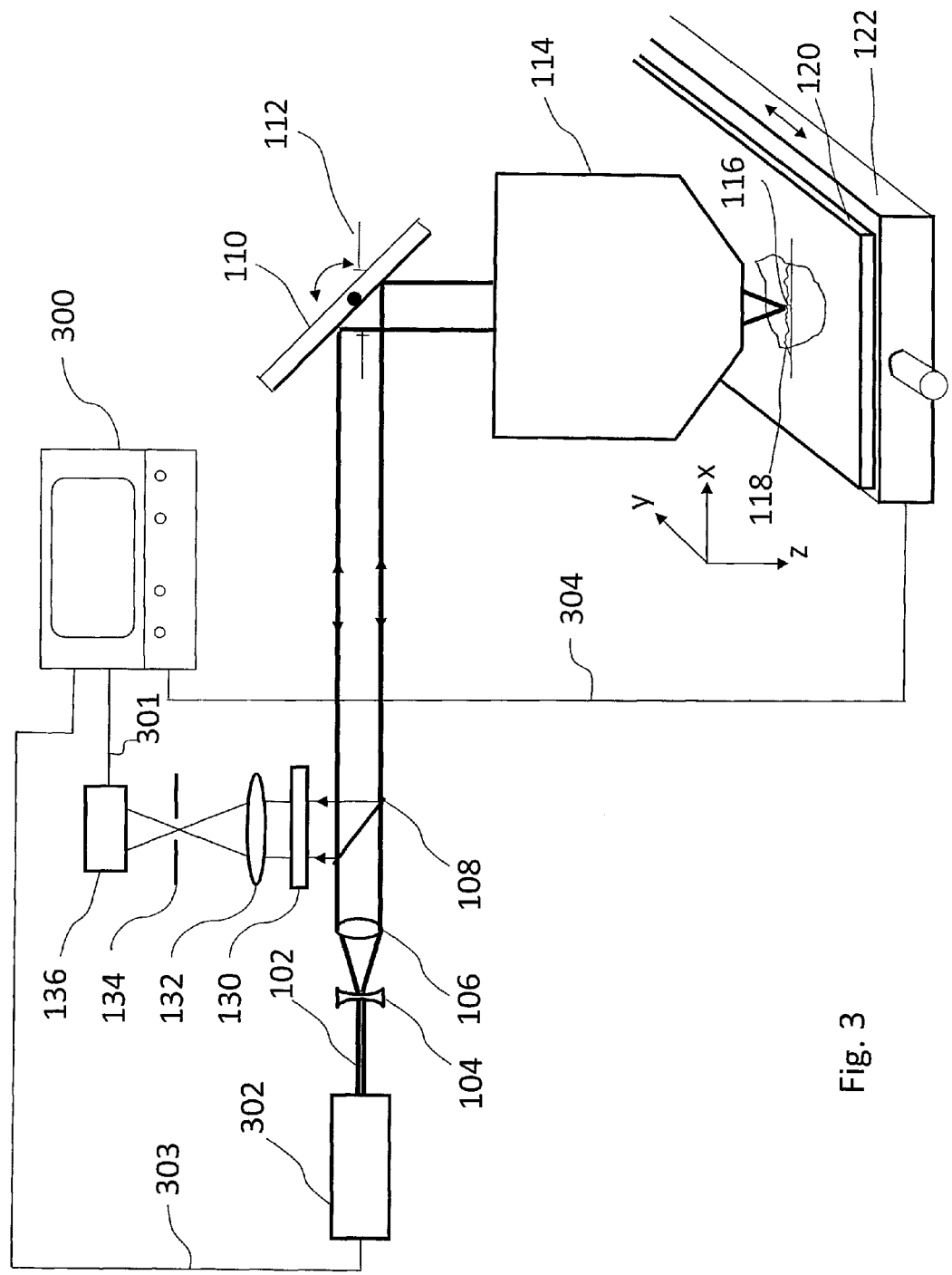
FIG. 3 is a schematic view of a scanning-beam/scanning-stage macroscope that is a first embodiment of this invention.

FIG. 3 shows a schematic view of a scanning-beam/scanning-stage macroscope that is a first embodiment of this invention. In this embodiment, a computer 300 is programmed to control the macroscope and to perform the steps described later in this document to acquire, store, process and display a fluorescence image with increased dynamic range. Computer 300 controls the power output of laser 302 through control cable 303. Collimated laser beam 102 from laser 302 passes through a beam expander (comprised of lens 104 and lens 106), and is expanded to match the diameter of entrance pupil 112 of laser scan lens 114 (note—entrance pupil 112 as indicated on the figure simply indicates the position of the entrance pupil. A real stop is not placed at this position). Scanning mirror 110 deflects the beam in the X direction. Laser scan lens 114 focuses the beam to focal spot 116 on specimen 118, mounted on microscope slide 120, and light reflected from or emitted by the specimen is collected by laser scan lens 114, descanned by scanning mirror 110, and partially reflected by beamsplitter 108 into a confocal detection arm comprised of laser rejection filter 130, lens 132, pinhole 134, and detector 136. Detector 136 is located behind pinhole 134. Light reflected from or emitted by the specimen at focal spot 116 is collected by laser scan lens 114 and passes through pinhole 134 and is detected, but light from any other point in the specimen runs into the edges of the pinhole and is not detected. The scan mirror is computer-controlled to raster the focused spot across the specimen (this control connection is not shown in the diagram). At the same time, microscope slide 120, which is mounted on a motor-driven scanning stage 122 controlled by computer 300 through control cable 304, moves slowly in the Y direction. The combination of rapid beam scanning across the specimen while it is moved slowly in the perpendicular Y direction results in a raster-scan motion of focused-laser spot 116 across specimen 118. The computer 300, connected to detector 136 through second cable 301, stores and displays the signal from detector 136, and controls the detector gain. Computer 300 provides means for acquiring, processing, displaying and storing the signal from detector 136 and controls detector gain, the speed of scanning stage 122, the intensity of laser 302, and the speed of scan mirror 110. Fluorescence exposure is changed by varying the scan speed of scanning mirror 110 (which changes the dwell time of the focused laser beam on each pixel position on the specimen) and/or the intensity of the laser beam and/or by changing detector gain.

Figure 4:
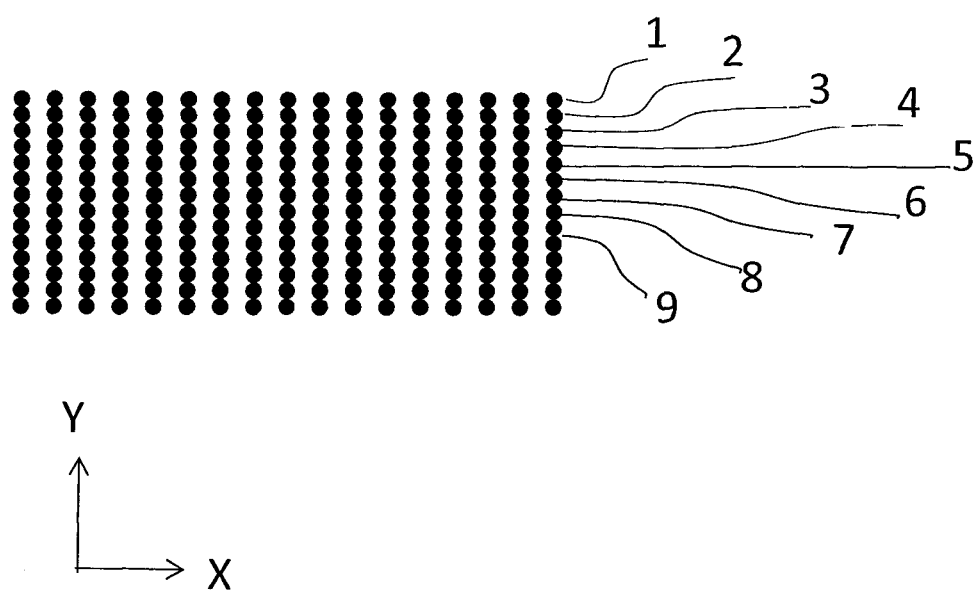
FIG. 4 shows an arrangement of pixel positions on part of a specimen in the first few scan lines as the scanning stage moves the specimen at constant speed in the Y direction.

FIG. 4 shows the arrangement of pixel positions on part of a specimen in a series of scan lines as scanning stage 122 moves in the Y direction. Note that the speed of the scanning stage has been adjusted so that the distance between pixels in the Y direction is half that in the X direction. The first nine scan lines are numbered from Scan line 1 to Scan line 9.

When using the instrument shown in FIG. 3 to produce a series of scan lines as shown in FIG. 4 the method of acquiring increased-dynamic-range images of fluorescent specimens is as follows:

1. First, a high-speed sparse-pixel preview scan (as described in PCT application WO 2009/137935 A1) is performed across the entire specimen (or the region of interest to be scanned), using a laser power that is small enough that no saturated pixels are expected in the preview scan image.
2. Next, using the histogram of pixel intensities calculated during acquisition of the preview image (or calculated from the preview scan image after acquisition), the laser power, speed of the scanning mirror (which constrains the pixel dwell time) and/or detector gain are adjusted so that the maximum pixel intensity expected in an image of the specimen is less than the maximum value for the dynamic range of the detector and A/D converter, but nearly fills the dynamic range of the detector and A/D converter. This combination of laser power, scanning mirror speed and detector gain results in a fluorescence image with no saturated pixels, however areas of weak fluorescence may not have good contrast with some signals lost in the noise. This preview image can also be used to estimate the increase in exposure that will be necessary to image areas of weak fluorescence with good contrast.
3. Scan line 1: Using the mirror scanner, move the focused laser spot across the specimen and collect data from pixel positions in the first scan line, moving from left to right in FIG. 4.
4. Scan line 2: Move the scanning stage in the Y direction a distance equal to half the distance between pixel positions on the specimen, increase the laser power and/or the detector gain, and scan the second scan line. If the combination of laser power and/or detector gain is increased by a factor of four (increasing the intensity of fluorescence from each pixel position in the specimen by approximately a factor of four) then this scan line will include saturated pixels in the areas where fluorescence intensity is high, but exposure in areas of weak fluorescence will be much better. (A factor of four is used as an example only—other factors also work well. The factor should be chosen to give good signal strength in areas of weak fluorescence.)

5. Scan line 3: Move the scanning stage a distance in the Y direction equal to half the distance between pixel positions on the specimen, return the laser power and detector gain to the settings used for Scan line 1, and acquire Scan line 3.

6. Add the value stored in the memory location for the first pixel in line one to the value stored in the memory location for the first pixel in Scan line 3, and divide the result by two. Continue on a pixel-by-pixel basis, until all pixels in Scan lines 1 and 3 have been averaged. Multiply the pixel values in this averaged line of pixels by a factor f. A method of estimating the value off is described in the discussion of FIG. 10. Note: The method described here can be modified by scanning the same strip in the specimen twice at different exposure values, while holding the stage stationary, which simplifies the combination of scan lines since odd-numbered lines do not have to be averaged as described here, but starting and stopping the moving stage can cause vibration in the microscope system.

7. Calculate the first line of data in the final image as follows:
   a. If the first pixel in Scan line 2 has a value less than saturation (<S), place that value in the first memory location in the increased-dynamic-range data store for Image line 1, or
   b. If the first pixel in Scan line 2 is equal to or greater than saturation (>/=S), place the value calculated for the first pixel in step 6 above into the first memory location in the increased-dynamic-range data store for Image line 1.
   c. Continue on a pixel-by-pixel basis, until the first line of increased-dynamic-range data is stored in the memory locations for the increased-dynamic-range data store for Image line 1.
   d. Note: A value of 0.9S has also been used successfully in 7(a) and 7(b).

8. Scan line 4: Move the scanning stage a distance in the Y direction equal to half the distance between pixel positions on the specimen, return the laser power and detector gain to the settings used for Scan line 2, and acquire Scan line 4.

9. Scan line 5: Move the scanning stage a distance equal to half the distance between pixel positions on the specimen, return the laser power and detector gain to the settings used for Scan line 1, and acquire Scan line 5.

10. Calculate the second line of data in the final image by averaging Scan lines 3 and 5, and combining the data with that in Scan line 4 in the same way as in step 7 above.

11. Continue until an entire strip of the specimen has been scanned, resulting in an image with increased dynamic range in which the relative intensities of pixels have been maintained across the entire image. Normally, calculations proceed during scanning, and the scanning stage moves at a constant speed (which is much slower than the motion of the focused laser spot across the specimen). In this method, twice as many scan lines are acquired as would be used for ordinary scanning imaging, but the dynamic range of the data is increased considerably.

12. For large specimens, two or more image strips can be stitched together to form an increased-dynamic-range image of the entire specimen.

Figure 12:
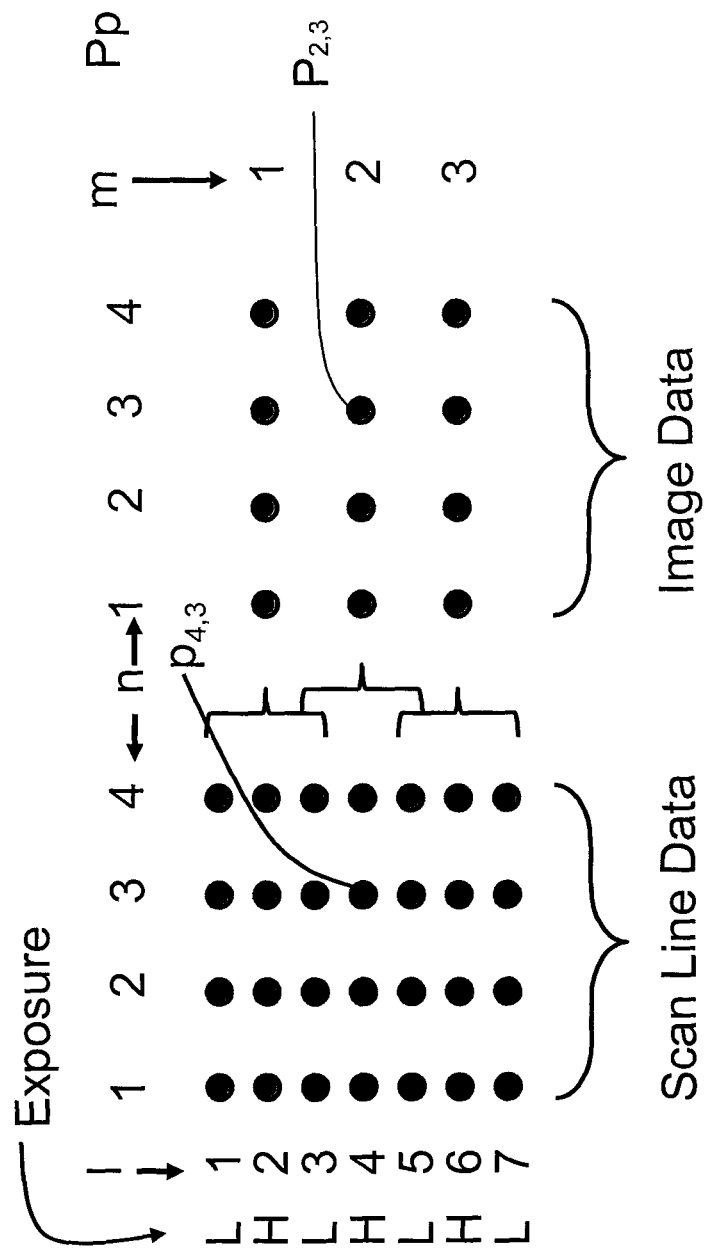
FIG. 12 is a schematic view of data from a series of linescans on the left which are combined using the method described in this document to produce the image data on the right.

FIG. 12 shows a schematic view of pixel positions on a series of scan lines on the left which are combined using the method described above to produce pixel values for the image data on the right. In FIG. 12 a series of seven scan lines each contain data from four pixel positions, with exposure alternating from low (L) to high (H) as the scan proceeds (left side of the figure). The number of pixel positions shown in this example is tiny compared to actual measurements, where a scan strip often contains 100,000 scan lines, with several thousand pixels in each scan line. Steps 7 through 11 above can be described mathematically as follows. Assume the saturation value at a pixel measurement position in the Scan Line Data is S, f is the multiplication factor described above, l is the scan line number, n is the pixel number in each scan line (and in each row of the final image) and m is the row number in the final image. The resulting image will contain n×m pixels, and is generated using 2m+1 scan lines (in this simplified small example, a 3×4 pixel image is created from l=2m+1=7 scan lines. Let $P_{m,n}$ be the image pixel value at position m,n in the final image, and $p_{m,n}$ be the measurement pixel value at position m,n in the scan line data.

As an example, consider the calculation of the value of image pixel $P_{2,3}$ on the right side of FIG. 12. The value of that pixel will equal the value of scan line pixel $p_{4,3}$ if that pixel is not saturated, or else it will equal the mean of the value of scan line pixel $p_{3,3}$ and scan line pixel $p_{5,3}$, multiplied by f. A method of calculating f is described later in this patent document. Mathematically, this can be written:

IF $p_{4,3} < S$, then $P_{2,3} = p_{4,3}$

IF $p_{4,3} \geq S$, then $P_{2,3} = \{(p_{3,3} + p_{5,3})/2\} * f.$

More generally,

IF $p_{2m,n} < S$, then $P_{m,n} = p_{2m,n}$

IF $p_{2m,n} \geq S$, then $P_{m,n} = \{(p_{(2m-1),n} + p_{(2m+1),n})/2\} * f.$

The values for pixels in the first line of the image can be calculated after the first three scan lines have been completed (and while the scan continues) by calculating values for each value of n (from n=1 to n=number of pixel positions measured in each scan line) where for the first line of the image m=1, and additional lines in the image can be calculated after every two additional scan lines are acquired, until that image strip is completed.

The method for increased-dynamic-range fluorescence imaging described above can be modified by scanning each specimen strip twice, once at a first fluorescence exposure, and a second scan at a second fluorescence exposure. In this situation a first strip image is acquired at fluorescence exposure in which no pixels in the image are saturated, and a second strip image is acquired with increased exposure that gives good contrast in areas with weak fluorescence, and the two strip images are combined on a pixel-by-pixel basis using the multiplying factor f estimated using all of the pixels in the two images (or using a multiplying factor f estimated using sparse-pixel preview images acquired with the same exposures as the two strip images). The resulting increased-dynamic-range image has a dynamic range that is larger than that of the detection system of the instrument, and relative pixel intensities are preserved across the image. This method has the advantage of not requiring the averaging of pixel values in odd-numbered scan lines (as described in Step 6 above) but the two strip images must be registered to a fraction of a pixel before combination.

The instrument described above is a scanning-beam/scanning-stage laser macroscope. A scanning-beam/scanning-stage laser microscope can also be used, with the disadvantage of having a smaller field of view and shorter length of scan line, which requires more strips to be acquired if the same specimen area is imaged and a considerable increase in scan time, however with the advantage of being able to use microscope objectives which are available with higher Numerical Aperture than scan lenses, resulting in higher resolution. The high-speed preview scan can also be used with a scanning-beam/scanning-stage microscope. In both cases, other light sources can be used in place of lasers.

The method for increased-dynamic-range fluorescence imaging described above can be modified for use in a confocal scanning laser microscope or macroscope in which there is no scanning stage but where the beam is scanned in both directions. In this situation a first image is acquired at fluorescence exposure in which no pixels in the image are saturated, and a second image is acquired with increased exposure that gives good contrast in areas with weak fluorescence, and the two images are combined using the method described above on a pixel-by-pixel basis using the multiplying factor f estimated using all of the pixels in the two images (or from images of a small area of interest), instead of just the pixels in one scan line as described above. The result is an image with increased dynamic range, where the dynamic range of the image is larger than that of the detection system of the instrument, and relative pixel intensities are preserved across the image.

Two-photon or multi-photon imaging: The confocal macroscope shown in FIG. 3 can be modified easily for two-photon or multi-photon imaging, by replacing laser 302 with a laser producing short pulses (a femtosecond pulsed near-IR laser for example) and by using a larger pinhole (or removing the pinhole completely). Since a two-photon instrument does not require a confocal detector, a non-descanned detector can also be used, which could be mounted below the specimen for wide angle detection. The method for increased dynamic range detection described above can also be used for two-photon or multi-photon fluorescence macroscopy or microscopy.

Spectrally-resolved detection: When detector 136 in FIG. 3 is replaced by a spectrally-resolved detector (for example a spectrometer using a multi-anode pint) to detect fluorescence spectra from each pixel position, a separate increased-dynamic-range image can be acquired for each channel in the detector. There are a wide range of signal strengths in the different detector channels, and scanning alternate lines with increased exposure and combining adjacent lines to increase the dynamic range in the final image from each channel is very useful. When using a spectrally-resolved detector, the dynamic range of the image acquired in each detector channel can be contracted to fill a single dynamic range for display (for example all images can be contracted to fill an 8-bit dynamic range) and the contraction information stored as metadata with each image. This would allow comparison of signal strength on a pixel-by-pixel basis inside each image, and using the metadata, between the images, while allowing easy storage and display of the multiple images. The method of achieving increased-dynamic-range imaging described herein is useful in both confocal scanning laser macroscopy and microscopy.

Figure 5:
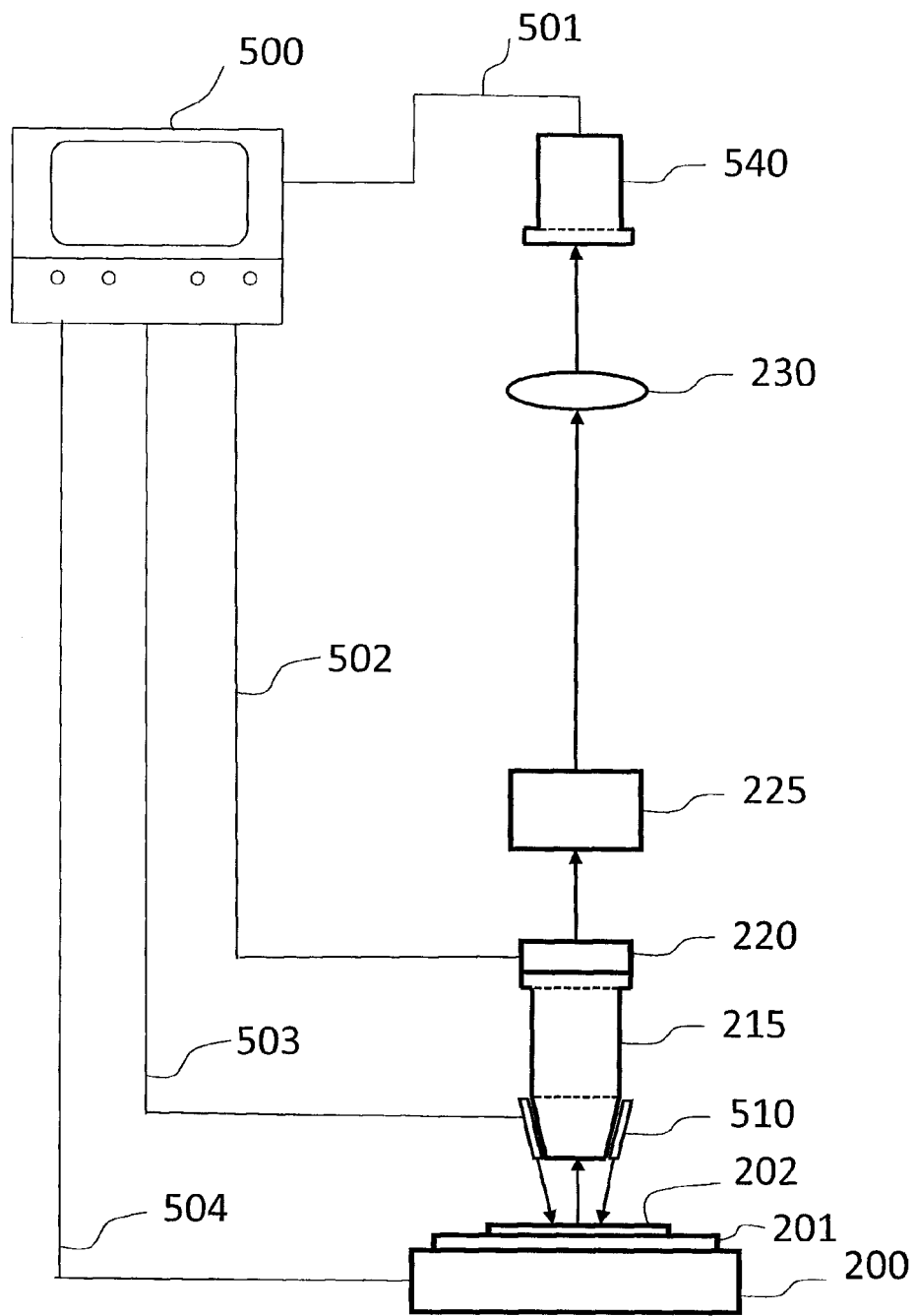
FIG. 5 is a schematic view of a microscope slide scanner that is a second embodiment of this invention.

FIG. 5 shows a schematic view of a scanning optical microscope using a linear array detector (or a TDI detector) that is a second embodiment of this invention. In this embodiment, a tissue specimen 202 (or other specimen to be imaged) mounted on microscope slide 201 is illuminated from above by illumination source 510, whose power output (and sometimes wavelength) is controlled by computer 500 through control cable 503. In fluorescence imaging the illumination source is usually mounted above the specimen (epifluorescence) so that the intense illumination light that passes through the specimen is not mixed with the weaker fluorescence emission from the specimen, as it would be if the illumination source were below the specimen. (Several different optical combinations can be used for epifluorescence illumination—including illumination light that is injected into the microscope tube between the microscope objective and the tube lens, using a dichroic beamsplitter to reflect it down through the microscope objective and onto the specimen.) A narrow wavelength band is chosen for the illumination light to match the absorption peak of the fluorophore in use. Fluorescence emitted by the specimen is collected by infinity-corrected microscope objective 215 which is focused on the specimen by piezo positioner 220, controlled by computer 500 through control cable 502. Emission filter 225 is chosen to reject light at the illumination wavelength and to pass the emission band of the fluorophore in use. The microscope objective 215 and tube lens 230 form a real image of the specimen on linear array detector 540 (containing an electronic shutter, not shown), which is read out by computer 500 through control cable 501. An image of the specimen is collected by moving the microscope slide at constant speed using motorized stage 200 (controlled by computer 500 through control cable 504) in a direction perpendicular to the long dimension of the linear array detector 540, acquiring a sequence of equally-spaced line images like those shown in FIG. 4. Line images are acquired each time the specimen moves a distance that causes the real image to move half the distance between individual pixels in the linear array detector and the illumination intensity is varied so the odd-numbered lines have lower exposure, and the even-numbered lines have increased exposure.

When using the instrument shown in FIG. 5 to produce a series of scan lines as shown in FIG. 4, and for example using a high illumination intensity that is four times the low illumination intensity, the method of acquiring increased-dynamic-range images of fluorescent specimens is as follows:

1. When a linear array detector is used, it is not possible to perform a high-speed preview scan of the entire specimen like that possible with a scanning beam/scanning stage macroscope or microscope as described in the first embodiment. In this second embodiment, the initial exposure can be estimated by imaging the entire specimen (or the area of interest), by imaging a small representative area of the specimen, or by collecting linescan data at a number of positions along the scan strip. The exposure for each line of the image will depend on the shutter speed (or exposure time) for each line image (which is constrained by the speed of stage motion), and the illumination intensity.

2. Next, adjust the illumination intensity, speed of the stage motion and shutter speed such that the maximum pixel intensity expected in an image of the specimen is less than the maximum value for the dynamic range of the detector and A/D converter, but nearly fills the dynamic range of the detection system. This is a good first gain setting for fluorescence imaging because no pixels would be saturated if the entire image were acquired with this setting, however areas of weak fluorescence may not have good contrast with some signals lost in the noise.

3. Start the stage scan using the scan speed (and shutter speed) estimated in step 1.

4. Scan line 1: Using the linear array detector, open and close the shutter to acquire data from pixel positions in the first scan line in FIG. 4. The shutter should remain open as long as possible as the stage moves half the distance between pixel positions on the specimen.

5. Scan line 2: When the scanning stage has moved a distance equal to half the distance between pixel positions on the specimen, increase the illumination intensity, and collect the second line of data. If the illumination intensity is increased by a factor of four (increasing the signal intensity of each pixel by a constant factor $f_4$) then this scan line will include saturated pixels in the areas where fluorescence intensity is high, but exposure in areas of weak fluorescence will be much better than in Scan line 1. (Increasing the illumination intensity by four is an example only—the value chosen depends on the particular situation).

6. Scan line 3: Move the scanning stage a distance equal to half the distance between pixel positions on the specimen, return the illumination intensity to the settings used for Scan line 1, and acquire Scan line 3.

7. Add the value stored in the memory location for the first pixel in line one to the value stored in the memory location for the first pixel in Scan line 3, and divide the result by two. Continue on a pixel-by-pixel basis, until all pixels in Scan lines 1 and 3 have been averaged. Multiply the pixel values in this averaged line of pixels by a factor $f_4$, which results in a line of data with approximately four times the intensity values of Scan line 2, and at the same position as Scan line 2. A factor of four is equivalent to increasing the dynamic range of the digital data by 2 bits. NOTE: since fluorescence intensity does not increase linearly with illumination intensity, the value of $f_4$ should be estimated using data like that shown in FIG. 10.

8. Calculate the first line of data in the final image as follows:
    a. If the first pixel in Scan line 2 has a value less than the saturation value S, place that value in the first memory location in the increased dynamic range data store for Image line 1, or
    b. If the first pixel in Scan line 2 is equal to or greater than the saturation value S, place the value calculated for the first pixel in step 7 above into the first memory location in the increased dynamic range data store for Image line 1.
    c. Continue on a pixel-by-pixel basis, until the first line of increased-dynamic-range data is stored in the memory locations for the increased-dynamic-range data store for Image line 1. Note: A value of 0.9S has also been used successfully in 7(a) and 7(b).
    d. Note: If blooming is a problem when saturated pixels are imaged by the linear array, then values for pixels adjacent to saturated ones should be chosen from the lower-intensity/gain data.

9. Scan line 4: Move the scanning stage a distance equal to half the distance between pixel positions on the specimen, return the illumination intensity to the settings used for Scan line 2, and acquire Scan line 4.

10. Scan line 5: Move the scanning stage a distance equal to half the distance between pixel positions on the specimen, return the illumination intensity to the setting used for Scan line 1, and acquire Scan line 5.

11. Calculate the second line of data in the final image by averaging Scan lines 3 and 5, and combining the data with that in Scan line 4 in the same way as in steps 7 and 8 above.

12. Continue until an entire strip of the specimen has been scanned, resulting in an image with increased dynamic range in which the relative intensities of pixels have been maintained across the entire image. Normally, calculations proceed during scanning, and the scanning stage moves at a constant speed. In this method, twice as many scan lines are acquired as would be used for ordinary scanning imaging, but the dynamic range of the data can be increased considerably.

13. For large specimens, two or more image strips can be stitched together to form an increased-dynamic-range image of the entire specimen.

A TDI detector array is often used in fluorescence slide scanners, but because TDI arrays work by transferring charge from one row of pixels to the next in synchronism with the motion of a real image of the specimen across the array, and only the last line of data is read out after the corresponding line in the moving image has moved completely across the array, it is not possible to change illumination on a line-by-line basis as described above for linear arrays. If the dynamic range required for the final image is larger than that generated by the TDI array, a complete strip image must be acquired for each exposure, and the strip images combined on a line-by-line basis as described above, resulting in an increased-dynamic-range image. In this case, care must be taken if the high-illumination-intensity image includes pixels that are saturated enough that charge overflows into the surrounding pixels. In that situation, final-image data for pixels adjacent to saturated pixels in the high-illumination-intensity image should be calculated from low-illumination-intensity pixel data. This method of detecting and combining images with different illumination intensity preserves relative pixel intensities across the entire image and increases the dynamic range available in the image.

Figure 6:
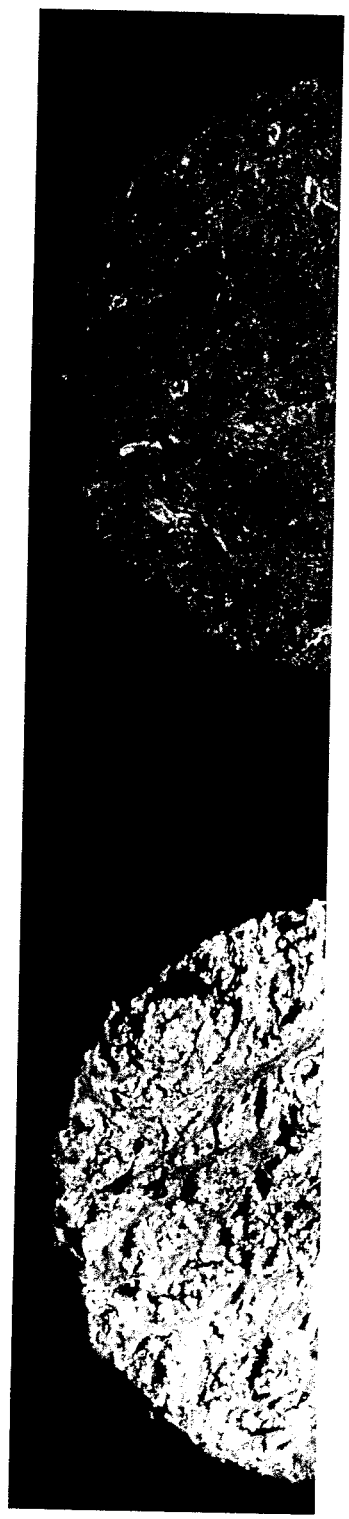
FIG. 6 shows a fluorescence image of a top half of two adjacent tissue specimens on a tissue microarray. The left specimen shows very strong fluorescence with many saturated pixels. The right specimen shows weak fluorescence with no saturated pixels.
Figure 7:
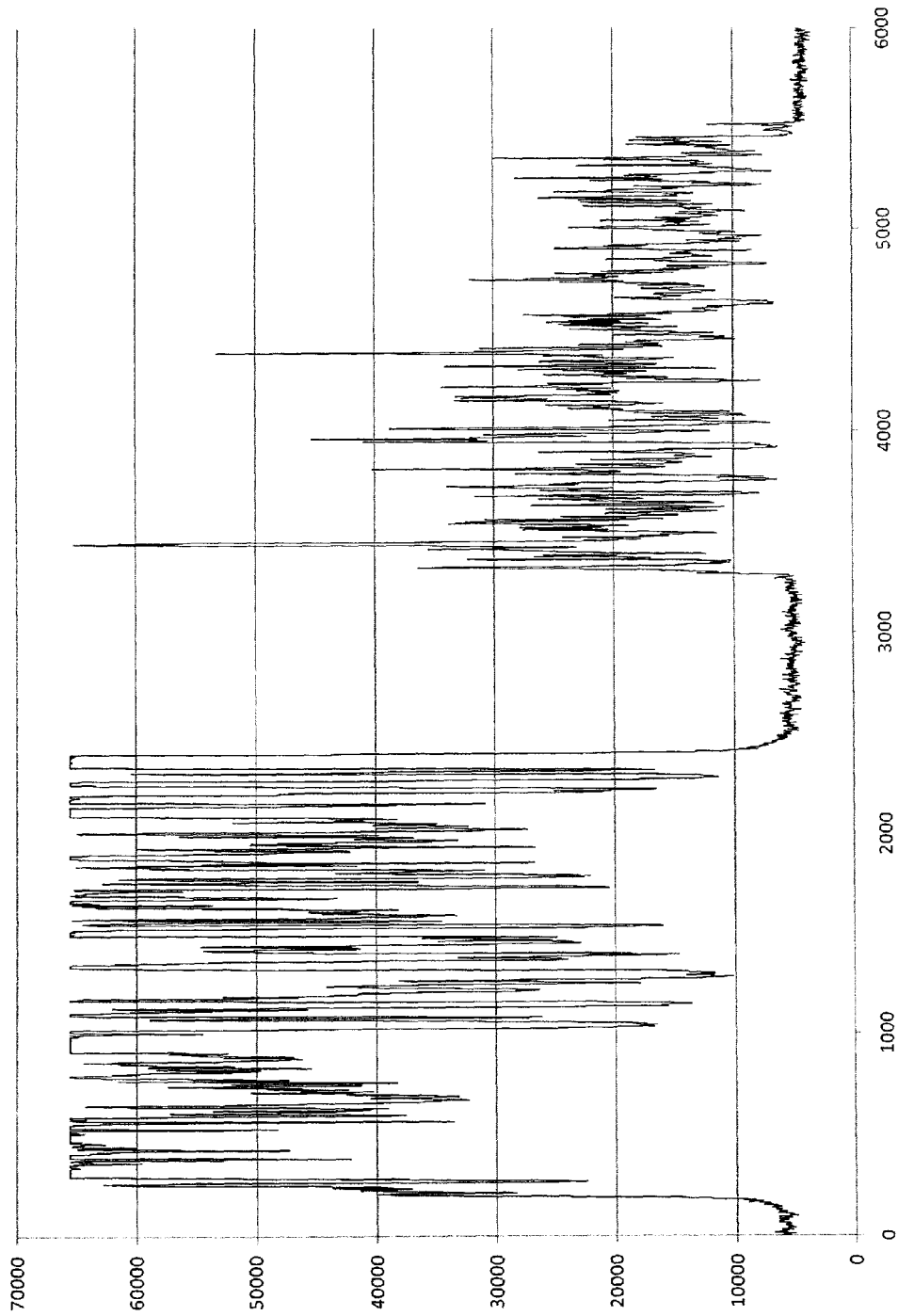
FIG. 7 shows a single fluorescence linescan (6000 pixels) across a bottom of the image shown in FIG. 6. Many pixels on a left side of the linescan are saturated.
Figure 8:
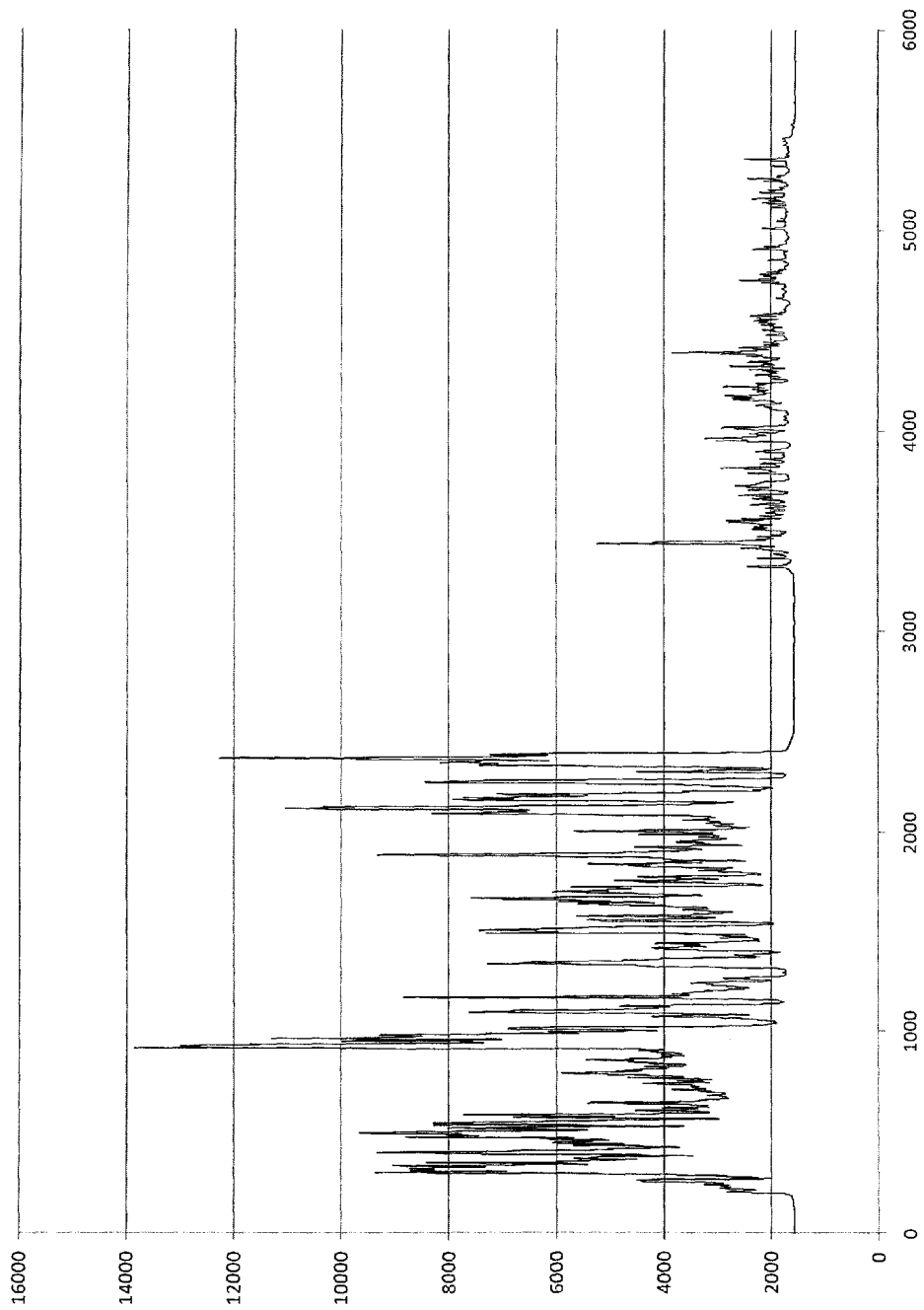
FIG. 8 shows a second scan along the same line on the specimen with reduced gain. No pixels are saturated.
Figure 9:
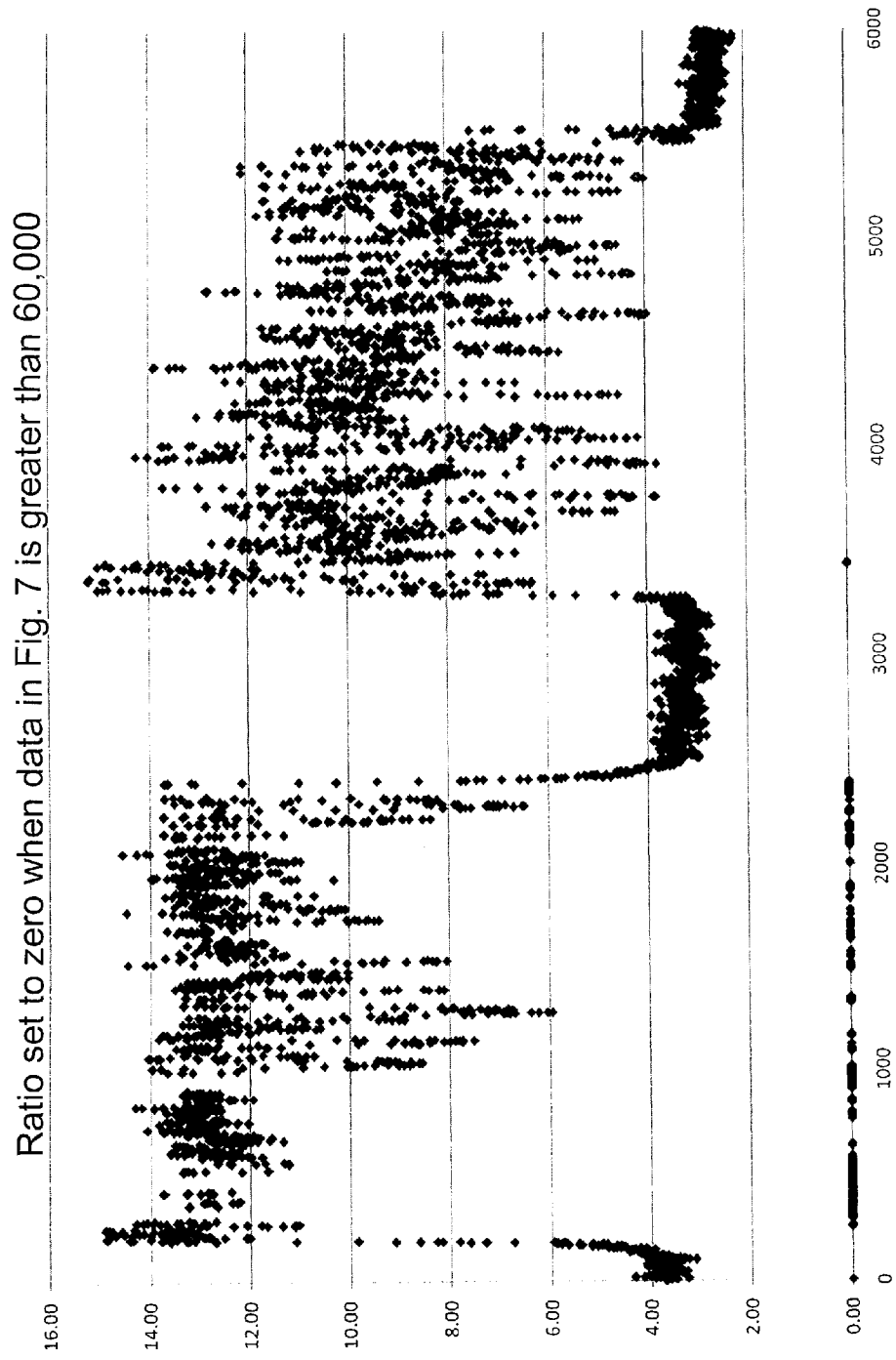
FIG. 9 shows the ratio of pixel intensity values in FIG. 7 to those in FIG. 8 on a pixel-by-pixel basis. The ratio is set to zero when pixel intensity values in FIG. 7 are greater than 60,000.
Figure 10:
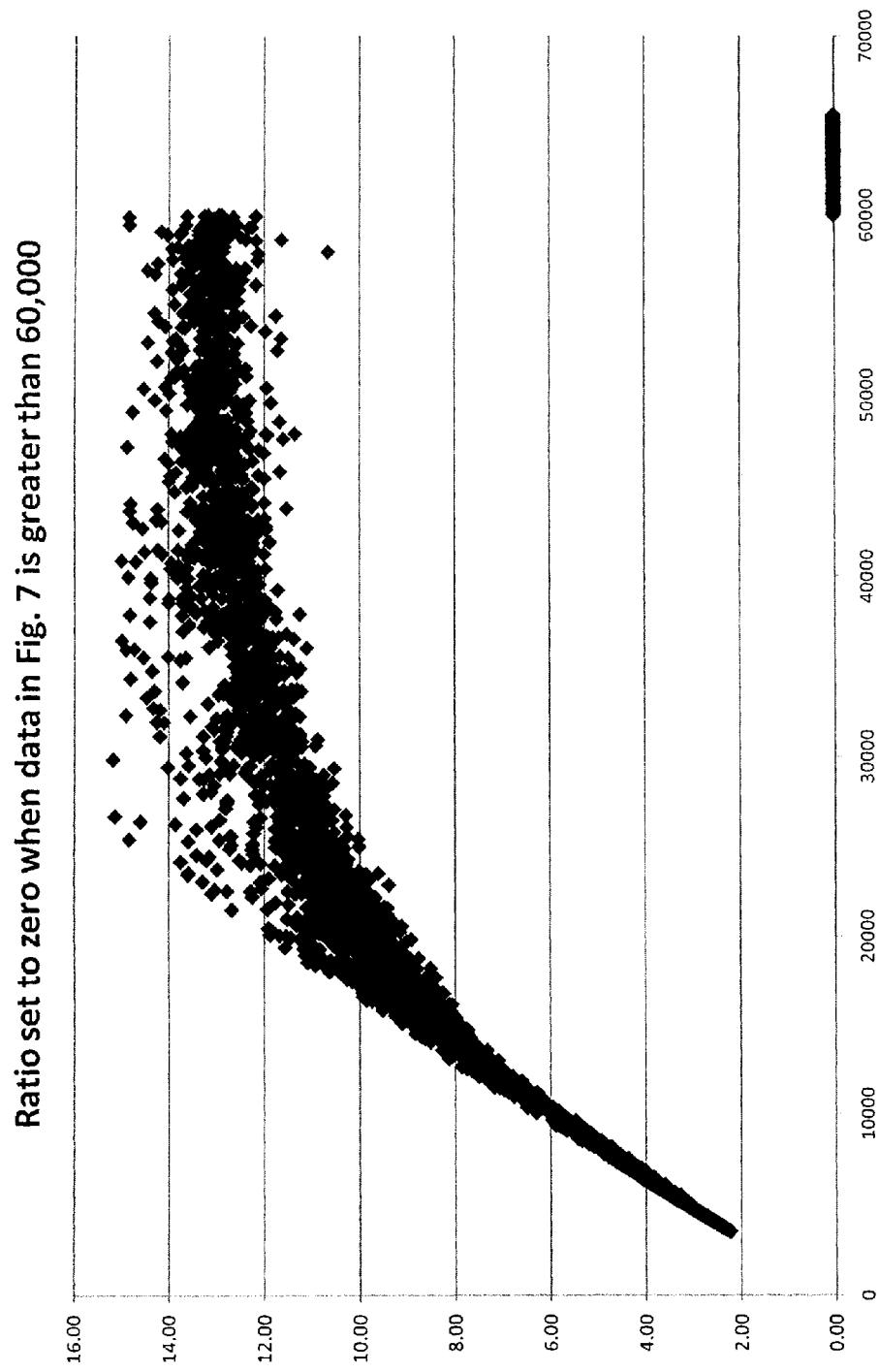
FIG. 10 shows the same data as in FIG. 9, but plotted as a function of the pixel intensity values of pixels in FIG. 7. The ratio has been set to zero when pixel intensity values in FIG. 7 were larger than 60,000.
Figure 11:
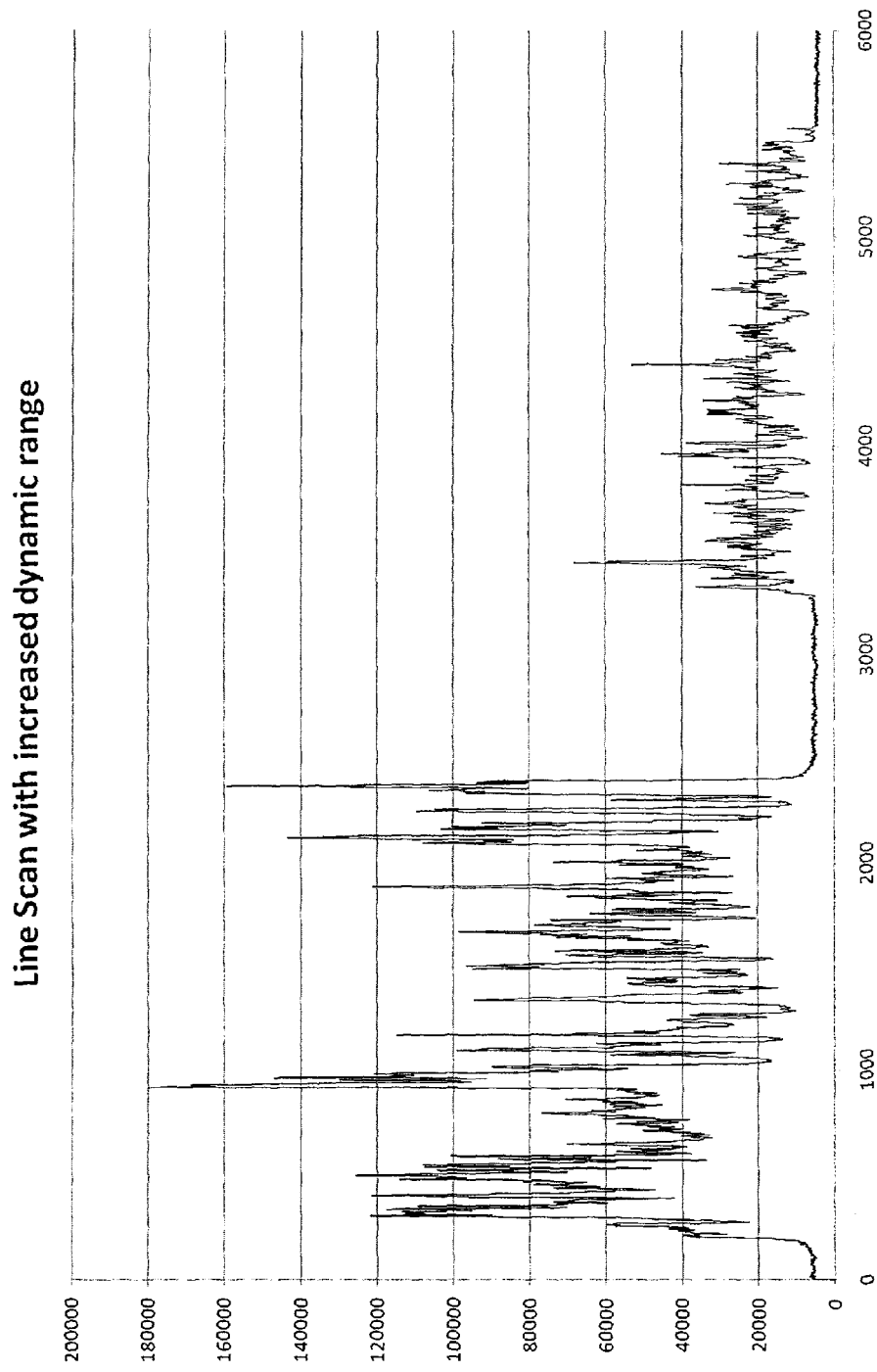
FIG. 11 shows linescan data with increased dynamic range after combining data in FIG. 7 with that in FIG. 8 using the method described in this document.

Example of the Method Using a Spot-Scanning Macroscope and Description of One Method for Estimating the Value of f:

One example of the method of producing increased-dynamic-range images using a scanning-beam/scanning-stage macroscope like that shown in FIG. 3 is as follows. FIG. 6 shows a fluorescence image of the top half of two adjacent tissue specimens on a tissue microarray. The specimen on the left has very bright fluorescence, and many pixels are saturated. The specimen on the right has weak fluorescence, and no pixels are saturated. FIG. 7 shows a single linescan containing 6000 pixels at the bottom of the image in FIG. 6, with pixel intensity values plotted on the vertical axis (from 0 to 65,535) and pixel positions from 0 to 6000 plotted on the horizontal axis. The dynamic range of the detection system is 16 bits, so pixels with an intensity value greater than 65,535 are saturated, and the pixel value recorded for saturated pixels is 65,535. Many pixels are saturated on the left side of this linescan. FIG. 8 shows a second scan across the same line on the specimen, but now with reduced detector gain (reduced pmt voltage in this case). The gain has been reduced considerably so that no pixels are close to saturation. The data in FIG. 8 will be used to replace saturated pixels in FIG. 7 by multiplying pixel values in FIG. 8 by a factor f. This factor can be estimated by calculating the ratio of pixel values in FIG. 7 and FIG. 8. This ratio is shown in FIG. 9. Because the ratio is meaningless when pixels in FIG. 7 are saturated, the ratio has been set to zero for all pixel values in FIG. 7 that are greater than 60,000 (saturated or nearly-saturated pixels). The calculated ratio is not a constant, and increases with increased pixel intensity values. FIG. 10 shows this same data, but plotted as a function of the pixel intensity values of the pixels in FIG. 7. Note that the ratio reaches a constant value at high pixel intensity values, and since only saturated (or nearly-saturated) pixels in FIG. 7 will be replaced by pixel values calculated using data in FIG. 8 (multiplied by this constant value), this constant value can be used for the multiplying factor. In this particular example, f=13. (The measurement of f is only required once for each specimen or area of interest, and the same value is used for the entire scan.) The resulting linescan, with saturated pixels in FIG. 7 replaced by pixel values in FIG. 8 multiplied by f, is shown in FIG. 11. All of the pixel values greater than 60,000 in FIG. 11 are values calculated using the pixel data in FIG. 8 multiplied by the factor calculated above, resulting in a linescan with (in this particular example) a maximum pixel value of 180,000.

A second method of calculating the value of f is to use the pixel data from two sparse-pixel preview scan images (instead of two linescans as described above), one acquired at an exposure level in which no pixels are saturated, and one acquired at an exposure level in which weak fluorescence signals are amplified so that there will be good contrast for weak fluorescence signals in the final image, but many pixels are saturated. The ratio f can be calculated by determining the ratio of pixel values at the same pixel positions in the two sparse-pixel images in the same way the ratio of pixel values was determined at the same pixel positions in the two linescan images in the description above.

In this example the dynamic range of the data has been increased from a maximum value of 14,000 to a maximum value of 180,000. It would have been possible to use the entire 16-bit dynamic range of the detection system (with a maximum value of 65,535) without using the method above, but only if fluorescence exposure were set perfectly in advance, which is almost impossible to do. In present practice, fluorescence exposure is usually estimated in advance and set to a low enough value to ensure that no pixels are saturated in the region of interest. The method described above can be used to easily increase the dynamic range of the data without requiring perfect exposure setting before imaging, and to increase the dynamic range of the data beyond that of the detection system of the instrument, with the result that relative pixel intensities are preserved across the entire image (or region of interest) and image detail is preserved and can be displayed in dark, mid-range and bright areas of the image.

We claim:

1. An instrument for scanning at least a part of a large specimen mounted on a specimen holder, the instrument comprising a light source, at least one lens to focus light from the light source, a detection system that comprises at least one detector, a computer programmed and configured to:
    a) take a plurality of measurements of each pixel at a plurality of exposure values;
    b) receive, process and store data received from the at least one detector;
    c) control a power output of the light source;
    d) control the movement of the specimen holder during scanning and a gain of the at least one detector to produce a digitized image of the at least one part of the specimen with a larger dynamic range than a dynamic range of the detection system
    e) an increased dynamic range of the instrument being sufficiently large to display image detail in dark, mid-range and bright areas of the image;
    f) the computer being programmed to combine scan lines to preserve relative pixel intensities across the entire image, the instrument being set up to scan the specimen in fluorescence; and
    g) acquire sequences of adjacent scan lines in which each scan line has an increased exposure value compared to an exposure value of the immediately previous scan line, the computer programmed to multiply pixel data from a first scan line by a factor and to combine pixel data from the first scan line and a second scan line to produce a single line of pixels in the final image comprised of pixel data from the first scan line multiplied by the factor whenever a pixel intensity value of any pixel in the second scan line is larger than a pre-determined amount and pixel data from the second scan line is used at or below the pre-determined pixel intensity value.

2. An instrument for scanning at least a part of a large specimen mounted on a specimen holder, the instrument comprising a light source, at least one lens to focus light from the light source, a detection system that comprises at least one detector, a computer programmed and configured to:
    a) take a plurality of measurements of each pixel at a plurality of exposure values;
    b) receive, process and store data received from the at least one detector;
    c) control a power output of the light source;
    d) control the movement of the specimen holder during scanning and a gain of the at least one detector to produce a digitized image of the at least one part of the specimen with a larger dynamic ran e than a dynamic range of the detection system;
    e) have a sequence of three different exposure values to be applied to successive scan lines, the data in a first scan line of the sequence being multiplied by a first factor, the data in a second line of the sequence being multiplied by a second factor and the data in a third line of the sequence being multiplied by a third factor, the factors being chosen to have the data fit an intensity curve of data values.

3. The instrument as claimed in claim 2 wherein the instrument is set up to scan the specimen in fluorescence.

4. The instrument as claimed in claim 1 wherein the increased dynamic range is sufficiently large to enable specimens on a plurality of microscope slides to be scanned without requiring changes in instrument set up before scanning each slide.

5. The instrument as claimed in claim 1 wherein the computer is programmed and configured to control movement of a scan mirror to raster scan the light source onto the specimen.

6. The instrument as claimed in claim 5 wherein the computer is programmed and configured to take high-speed preview scans of the entire specimen or an area of interest Where the preview scans are comprised of sparse pixel images of equally-spaced pixels that have the same size as corresponding pixels in the final image.

7. The instrument as claimed in claim 1 wherein the computer is programmed and configured to have each pixel scanned at two different exposure values in sequence while moving a scanning stage at a constant speed and averaging pairs of sequential odd-numbered scan lines on a pixel-by-pixel basis before combining the averaged odd-numbered scan lines with the even-numbered scan line located between the odd-numbered scan lines.

8. The instrument as claimed in claim 1 wherein an intensity of the light source is modulated during scanning whereby each line of data is scanned at a different intensity from immediately adjacent lines of data.

9. The instrument as claimed in claim 2 wherein the increased dynamic range of the instrument is sufficiently large to display image detail in dark, mid-range and bright areas of the image, the computer being programmed to combine scan lines to preserve relative pixel intensities across the entire image.

10. The instrument as claimed in any one of claims 2, 9, or 3 wherein there are a plurality of detectors used in the instrument.

11. The instrument as claimed in any one of claims 2, 9, or 3 wherein there is at least one linear array detector of the at least one detector and the computer is programmed and configured to determine exposure values using one or more line scans on the specimen or a scan of at least a part of the specimen.

12. The instrument as claimed in any one of claims 2, 9, or 3 wherein the instrument is set up and the computer is programmed and configured to scan the at least the part of a large specimen in spectrally-resolved fluorescence.

13. The instrument as claimed in any one of claims 2, 9, or 3 wherein there is image viewing software on a serving computer, the viewing software contracting individual image tiles in one or more regions of interest of the image, thereby enabling the one or more regions of interest of the image to be viewed using the dynamic range of a remote computer display While preserving the dynamic range of the entire image in an original file.

14. An instrument for scanning at least a part of a large specimen mounted on a specimen holder, the instrument comprising a light source, at least one lens to focus light from the light source, a detection system that comprises at least one detector, a computer programmed and configured to:
 a) take a plurality of measurements of each pixel at a plurality of exposure values;
 b) receive, process and store data received from the at least one detector;
 c) control a power output of the light source;
 d) control the movement of the specimen holder during scanning and a gain of the at least one detector to produce a digitized image of the at least one part of the specimen with a larger dynamic range than a dynamic range of the detection system, an increased dynamic range of the instrument is sufficiently large to display image detail in dark, mid-range and bright areas of the image, the computer programmed to combine scan lines to preserve relative pixel intensities across the entire image;
 e) contract dynamic range and to serve imaging tiles over a network where contraction of individual tiles is performed on a server before sending the image tiles out over the network and where dynamic range contraction is based on one or more regions of interest or on the entire image file, the instrument being capable of providing the desired dynamic range for viewing the image on a remote computer using the dynamic range of the remote computer display while preserving the dynamic range of the image data in the original file.

15. The instrument as claimed in claim 14 wherein the computer is programmed and configured to re-create or review a viewing session on the remote computer including a region of interest specification, dynamic range contraction parameters and information describing which tiles were served and the order of serving which is stored on the remote computer or on the server.

16. The instrument as claimed in any one of claims 14 or 15 configured to re-create or review a viewing session or a remote computer including colour space parameters.

17. The instrument as claimed in any one of claims 14, 15 or 16 wherein the computer is programmed and configured to:
 a) cause the instrument to scan a full strip at one exposure and to scan the identical strip at another exposure;
 b) combine the two images from the two scans into one digitized image of the at least part of the scanned specimen; and
 c) the digitized image having a larger dynamic range than a dynamic range of the detection system.

* * * * *